United States Patent
Kumar et al.

(10) Patent No.: US 8,057,643 B2
(45) Date of Patent: Nov. 15, 2011

(54) ECO-FRIENDLY PROCESS FOR RECOVERY OF PYRIDINE AND/OR ITS DERIVATIVES

(75) Inventors: Mahendra Kumar, Moradabad (IN); Sanjeev Kumar Dixit, Moradabad (IN); Shailendra Kumar Singh, Moradabad (IN); Ashutosh Agarwal, Moradabad (IN)

(73) Assignee: Jubilant Organosys Limited, Utter Pradesh (IN)

( * ) Notice: Subject to any disclaimer, the term of this patent is extended or adjusted under 35 U.S.C. 154(b) by 75 days.

(21) Appl. No.: 12/441,042

(22) PCT Filed: Nov. 17, 2006

(86) PCT No.: PCT/IN2006/000456
§ 371 (c)(1),
(2), (4) Date: Mar. 27, 2009

(87) PCT Pub. No.: WO2008/032334
PCT Pub. Date: Mar. 20, 2008

(65) Prior Publication Data
US 2010/0041894 A1 Feb. 18, 2010

(30) Foreign Application Priority Data

Sep. 12, 2006 (IN) .......................... 2021/DEL/2006

(51) Int. Cl.
*B01D 3/34* (2006.01)
*C07D 213/06* (2006.01)

(52) U.S. Cl. .............. 203/46; 203/60; 203/98; 546/246; 546/353

(58) Field of Classification Search .............. 203/45–46, 203/60, 98; 546/246, 353
See application file for complete search history.

(56) References Cited

U.S. PATENT DOCUMENTS

| 2,058,435 | A | | 10/1936 | Fisher et al. | |
| 4,237,300 | A | | 12/1980 | Bochis et al. | |
| 4,364,869 | A | * | 12/1982 | Muller et al. | 554/129 |
| 4,404,388 | A | * | 9/1983 | Fah et al. | 546/345 |
| 5,100,514 | A | | 3/1992 | Berg et al. | |
| 5,208,342 | A | * | 5/1993 | Gupton et al. | 546/116 |
| 5,364,941 | A | | 11/1994 | Yamakawa et al. | |
| 6,087,507 | A | | 7/2000 | Laitinen et al. | |
| 6,133,449 | A | | 10/2000 | Brightwell et al. | |
| 6,346,623 | B1 | | 2/2002 | Steinbauer et al. | |
| 6,939,972 | B2 | * | 9/2005 | Kumar et al. | 546/304 |
| 7,348,435 | B2 | * | 3/2008 | Kaushik et al. | 546/246 |

FOREIGN PATENT DOCUMENTS

| EP | 0 261 549 | 3/1988 |
| EP | 0 573 954 | 12/1993 |
| JP | 7 215939 | 8/1995 |

OTHER PUBLICATIONS

Vladimir N. Bulavka, et al., "Synthesis of 4-aminopyridine and 4-acetylaminopyridine by reduction of 4-nitropyridine-N-oxide with iron and mineral acids", Fourth International Electronic Conference on Synthetic Organic Chemistry, XP-002440537, http://pages.unibas.ch/mdpi/ecsoc-4/a0082/a0082.htm, 2000.

* cited by examiner

*Primary Examiner* — Virginia Manoharan
(74) *Attorney, Agent, or Firm* — Oblon, Spivak, McClelland, Maier & Neustadt, L.L.P.

(57) ABSTRACT

A process recovers of pyridine and/or its derivatives from their aqueous mass and/or manufacturing reaction mass by liquid-liquid extraction employing an alkyl acetate. The process further involves effective recovering and recycling of solvents from the aqueous phase and other waste obtained during the process.

9 Claims, No Drawings

ECO-FRIENDLY PROCESS FOR RECOVERY OF PYRIDINE AND/OR ITS DERIVATIVES

CROSS REFERENCE TO RELATED APPLICATIONS

The present application is the U.S. national stage of international application PCT/IN2006/000456, filed on Nov. 17, 2006, published as WO 2008/032334, the text of which is incorporated by reference, and claims the benefit of the filing date of Indian Application No. 2021/DEL/2006, filed on Sep. 12, 2006, the text of which is also incorporated by reference.

FIELD OF THE INVENTION

In general, this invention relates to the field of recovery of heterocyclic aromatic bases. More particularly the present invention provides an ecofriendly process for recovering pyridine and/or pyridine derivatives from their aqueous mass and/or manufacturing reaction mass employing a liquid-liquid extraction in the presence of an environmentally non-hazardous organic solvent.

BACKGROUND OF THE INVENTION

Pyridine and pyridine derivatives are effectively used as solvents and also as catalysts. They are used in the synthesis of many different products which are used as medicines, vitamins, food flavorings, paints, dyes, rubber products, adhesives, insecticides and herbicides.

The most general industrial synthetic reaction for the manufacture of pyridine bases is by the catalytic condensation of aldehydes and/or ketones with ammonia. The reaction is usually carried out at 350-500° C. and at atmospheric pressure in the presence of alumino-silicate catalyst. Acetaldehyde, formaldehyde (in the form of formalin), and ammonia are fed to a catalyst-containing reactor, where pyridine and alkyl pyridines are formed as the major product. A wide variety of catalysts, reactants, and reaction conditions are reported in known art. "Pyridine and Pyridine Derivatives", Goe, Gerald L., Kirk-Othmer, 3rd Edition, Vol. 19, John Wiley & Sons, p. 454 (1978); "Synthetic and Natural sources of the Pyridine Ring", Bailey et al., pp. 1-252 in "Heterocyclic Compounds", Volume 14, "Pyridine and Its Derivatives", John Wiley & Sons, New York (1984), all of which are incorporated by reference in their entirety herein.

Pyridine and pyridine derivatives present in the aqueous mass are extracted by suitable method. A wide variety of methods have been applied to the problem of the separation of pyridine and pyridine derivatives. The pyridine-water azeotrope has been separated in accordance with conventional techniques e.g., by conventionally breaking the water-pyridine azeotrope by the addition of suitable solvent followed by fractional distillation to prepare substantially dry pyridine. The solvent is recovered from pyridines by distillation and recycled back to the recovery column.

Several processes are disclosed in prior patent disclosures for the separation of pyridine or pyridine derivatives from aqueous solutions by using different solvents.

Benzene is most commonly used for the recovery of pyridine and picolines from the aqueous reaction mass. See ref. "Pyridine and Pyridine Derivatives" Shimizu et al p. 399 in "Ullman's Encyclopedia of Industrial Chemistry", Vol. A22, 5$^{th}$ Ed.; Elvers, B., Hawkins, S., Russey, W., Schulz, G., Eds., VCH Publishers, Weinheim (1993).

U.S. Pat. No. 4,883,881, discloses the process in which pyridine was separated from pyridine-water azeotrope by adding benzene thereto and distilling the resultant mixture to recover substantially anhydrous pyridine.

However, benzene loss during the process results in the concern like the cost of environmental protection measures, occupational safety, increased fire risks and additional investments in hazardous waste disposal costs. Besides, the use of benzene has been banned throughout a number of industries because of its hazardous nature. Therefore, there is an urgent need to address these issues, especially when the process is implemented at commercial scale.

U.S. Pat. No. 2,058,435 reported a process in which aqueous solutions of pyridine and its homologues are subjected to extraction with highly efficient extracting agents, which are non-solvents with respect to water. The process comprises the recovery of pyridine from its aqueous solution with any one of a number of solvents such as benzene, trichloroethylene, isopropyl ether, pseudo-cumene, cyclohexane, hexane and the like.

European Patent No. EP1,346,757 discloses liquid-liquid extraction with a solvent consisting of a fluorinated fluid selected from either hydrofluoropolyethers, hydrofluoroethers, hydrofluorocarbons and/or their mixtures with perfluoropolyethers and/or perfluorocarbons.

U.S. Pat. No. 5,100,514 describes a method for separating pyridine from water using certain organic compounds, as the agent in azeotropic or extractive distillation. Typical examples of effective agents are: by azeotropic distillation, methyl isoamyl ketone and propylene glycol dimethyl ether; by extractive distillation, isophorone and sulfolane.

Other conventional techniques can also be used, e.g., drying operations, extraction, saltation, redistillation, etc., in accordance with fully conventional considerations, e.g., as discussed in any of a wide variety of relevant texts, e.g., see ref. "Chemist's Companion", Gordon, Arnold J. et al., John Wiley and Sons (1972).

Park, Choon Ho. et al in Journal of Applied Polymer Science (1999), 74(1), 83-89, has discussed the pervaporation separation through a poly(acrylonitrile-co-vinylphosphonic acid) membrane. Polyacrylonitrile (PAN)-based copolymers containing phosphonic acid moiety were synthesized for dehydration of aqueous pyridine solution. The in situ complex, formed between the vinylphosphonic acid (VP) moiety in the membrane and the pyridine in the feed, enhanced separation capacity of poly(acrylonitrile-co-vinylphosphonic acid) (PANVP) membranes. All the PAN-based membranes containing phosphonic acid were very selective toward water. The pervaporation performances of PANVP membranes depended on the content of the phosphonic acid moiety in the membrane and operating temperature. The pervaporation separation of water/pyridine mixtures using PANVP membranes exhibited over 99.8% water concentration in permeate and flux of 4-120 $gm^{-2}h^{-1}$ depending on the content of vinylphosphonic acid and operating temperature.

U.S. Pat. No. 6,087,507 describes a method of continuously separating pyridine or pyridine derivatives from aqueous solutions by extraction, wherein supercritical fluid is employed to extract the pyridine material from liquid media. The method of the invention, in particular, extracts pyridine or pyridine derivatives from aqueous solutions with pressurized carbon dioxide, which is used under pressure, or in the liquid state, or in the near critical state or in the supercritical state. The operating system is a continuously operating extraction system, so that a part, or all, of the pyridine and/or pyridine derivatives are transferred from the aqueous phase to the carbon dioxide phase, and thereafter the aqueous phase and carbon dioxide phase are separated from each other; and the pyridine and/or pyridine derivatives are separated from carbon dioxide; and the extract containing pyridine and/or pyridine derivatives is thereby obtained. Preferred temperatures for the pyridine and/or pyridine derivative contacting with carbon dioxide are from 5 to 80° C.; and preferred pressures range from 60 to 300 bar. However, the process is not suitable at, industrial scale because extraction was done at very high pressure (60 to 300 bar). This makes extraction process operationally unfriendly and highly capital intensive at industrial scale.

The processes disclosed in the prior art used hazardous and industrially unsuitable solvents. Some of the solvents disclosed are highly unsafe to handle in commercial scale manufacturing processes. Moreover most of the processes discussed in prior art are for the separation of pyridine or pyridine derivatives from aqueous solutions only, not from the complex manufacturing reaction mass. The problems associated with the above prior art can be overcome by using commercially viable; operational and eco-friendly process and solvent to avoid all the above-mentioned problems in the known prior art.

SUMMARY OF THE INVENTION

It is, therefore, an object of the present invention to improve upon limitations in the prior art, wherein the invention provides an improved process for recovery of pyridine and/or its derivatives from their aqueous mass and/or manufacturing reaction mass employing a liquid-liquid extraction in the presence of a selective organic solvent, which is environmentally non-hazardous.

Another object of the present invention is to provide an eco-friendly process for recovering pyridine and/or its derivatives, wherein the process effectively recovers and recycles solvents from the organic phase, aqueous phase and from the other waste obtained during the process, which makes process cost efficient.

Yet another object of the present invention is to provide an eco-friendly process for recovering pyridine and/or its derivatives, wherein said process is capable of recovering said pyridine and/or its derivatives from its manufacturing reaction mass and wherein said manufacturing reaction mass comprises pyridine, beta picoline, ammonia, aliphatic amines, aldehyde and aldehyde based organic impurities, other monoalkyl pyridines, dialkyl pyridines, trialkyl pyridines or unidentified heavy organic materials.

Another object of the present invention is to provide an eco-friendly and cost efficient process for recovery of pyridine and/or its derivatives, wherein said object of the invention is achieved by employing a suitable solvent which is environmentally non-hazardous selected from Class III solvent as per ICH guidelines and effectively managing to recover and recycle said solvent in the process.

Yet another object of the present invention is to select a suitable organic solvent and employing the same in recovery process of pyridine and/or its derivatives from their aqueous mass and/or its manufacturing reaction mass by liquid-liquid extraction, wherein said solvent is non-toxic, environmentally acceptable and miscible with aqueous medium as compared to solvents used in prior art.

These and other objects are attained in accordance with the following embodiments, the particular embodiments hereinafter described in accordance with the best mode of practice, however the present invention is not restricted to the particular embodiments.

In accordance with the preferred embodiment of the present invention, there is provided an eco-friendly process for recovering pyridine and/or its derivatives from aqueous mass and/or its manufacturing reaction mass, the process comprising treating said mass with an organic solvent, separating the resultant organic phase and aqueous phase and distilling said organic phase to obtain pyridine and/or its derivatives and a part of said organic solvent, wherein said aqueous phase and the other waste obtained during the process is distilled and esterified to additionally recover said organic solvent and recycled in the process.

In accordance with one preferred embodiment of the present invention, there is provided an eco-friendly process for recovering pyridine and/or its derivatives employing an organic solvent which is environmentally non-hazardous, wherein the process comprises recovering ammonia from the manufacturing reaction mass containing pyridine and/or its derivatives along with other low boiling and high boiling by-products and ammonia, extracting resultant aqueous mass containing pyridine and/or its derivatives employing said solvent, separating the organic phase, formed by said solvent containing pyridine and/or its derivatives, from the aqueous phase, and recovering pyridine and/or its derivatives from the organic phase by fractional distillation.

In accordance with one other embodiment of the present invention, there is provided an eco-friendly process for recovering pyridine and/or its derivatives employing an organic solvent, wherein said solvent is environmentally non-hazardous solvent selected from Class III solvent as per ICH guidelines.

In accordance with yet another embodiment of the present invention, there is provided an eco-friendly process for recovering pyridine and/or its derivatives employing an organic solvent, wherein said solvent is selected preferably from alkyl acetate.

In accordance with yet another embodiment of the present invention, there is provided an eco-friendly process for recovering pyridine and/or its derivatives employing said organic solvent alkyl acetate, wherein said process effectively recovers and recycles said solvent additionally from the aqueous phase and from the other waste comprising part of said alkyl acetate and corresponding alkanol obtained during the process.

In accordance with yet another embodiment of the present invention, there is provided an eco-friendly process for recovering pyridine and/or its derivatives employing an environmentally non-hazardous organic solvent, wherein the process comprises recovering the used solvent in the process during distillation of extracted organic mass and reusing the same in the recovery process of pyridine and/or its derivatives.

In accordance with still another embodiment of the present invention, there is provided an eco-friendly process for recovering pyridine and/or its derivatives employing an alkyl acetate, wherein the process comprises esterifying the resultant alkanol produced by hydrolysis of alkyl acetate and recovering the same along with unreacted alkyl acetate and reusing in the process.

In accordance with still another embodiment of the present invention, there is provided an eco-friendly process for recovering pyridine and/or its derivatives employing an alkyl acetate, wherein the process effectively recovers the respective alkanol, which is degraded due to highly alkaline system and reusing the same upon resterification in the process.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included examples.

Nowadays with increasing ecological problems viz., pollution, global warming, etc., the emphasis in industries is not only on economical process but also on green processes. Thus, in present scenario it has become a need to combine economic and ecological principle in any process development. Accordingly, these objects are accomplished by the present invention, which in its broadest aspects provides an extraction process for pyridine and/or its derivatives from aqueous mass and or its manufacturing reaction mass without using highly hazardous solvents like benzene and highly capital intensive and operationally unfriendly process like using carbon dioxide.

The disclosed embodiment of the present invention deals with a process for the recovery of pyridine and/or its derivatives that have advantage as it avoids handling of unsafe solvent like benzene and also effectively recycle the solvent used in the recovery. Moreover, the present process involves utilization of industrially suitable solvent to make it comparatively safe, more operational friendly and economical. Thus, the present invention addresses the disadvantages and complications associated with the processes heretofore disclosed.

According to the present invention, there is provided a process of recovering pyridine and pyridine derivatives from aqueous mass and or its manufacturing reaction mass using alkyl acetate (Class III solvent as per ICH guidelines) as a substitute to hazardous solvent like benzene (Class I solvent as per ICH guidelines). Alkyl acetate as solvents are non-toxic and environmentally acceptable as compared to benzene. The use of alkyl acetate for the recovery of pyridine and pyridine derivatives reduces the environmental hazards, cost involved in the environmental protection measures, increase occupational safety and bring savings in hazardous waste disposal cost, apart from direct investment gains.

According to the present invention there is provided a process for the recovery of pyridine and/or pyridine derivatives from aqueous mass and/or its manufacturing reaction mass with an eco-friendly solvent, which is an excellent solvent for pyridine and its derivatives but is substantially a non-solvent with respect to water. After the extraction is completed, the resulting extract is subjected to fractional distillation, which completely removes the solvent and leaves the pyridine and/or pyridine derivatives in substantially anhydrous condition.

According to the present invention, the process used herein capable of isolating pyridine and/or its derivatives in substantially anhydrous condition from its aqueous mass and/or its manufacturing reaction mass. The "manufacturing reaction mass" used herein is meant to refer the reaction mass is obtained during manufacturing of pyridine and/or its derivatives, wherein said manufacturing mass may comprise pyridine, beta picoline, ammonia, aliphatic amines, aldehyde and aldehyde based organic impurities, other monoalkyl pyridines, dialkyl pyridines, trialkyl pyridines or other unidentified heavy organic materials. The "aqueous mass" used herein is meant to refer to any stream containing pyridine and/or its derivatives essentially in water and not a manufacturing reaction mass.

The disclosed preferred embodiment of the present invention describing a process for the separation of pyridine and/or pyridine derivatives from aqueous mass and/or its manufacturing reaction mass can be more readily understood through reading the following detailed description of the invention and the process Flow diagram.

The present invention provides an improved process for the preparation of pyridine and pyridine derivatives comprising first recovering ammonia from the manufacturing reaction mass under atmospheric pressure maintaining pot temperature 85-95° C. to achieve minimum possible ammonia in the reaction mass (desirable <1.6%) as the higher amount of ammonia reduces the solvent recovery and hence the process economics. The recovery can also be performed under vacuum.

The reaction mass obtained after ammonia recovery is extracted with an organic solvent preferably alkyl acetate. The alkyl acetate used herein is preferably selected from ethyl acetate, n-propyl acetate, isopropyl acetate, methyl acetate, etc. Preferred is ethyl acetate. The recovery can be done in a batch extraction system or in a continuous extraction system. The reaction mass containing pyridine and picolines in addition to other high boiling pyridine bases and some low boiling constituents is agitated with the solvent by any known prior art process. After agitating for about 30 minutes at room temperature, agitation is stopped to separate out the two layers. The aqueous layer is analyzed for pyridine and picoline content. This process is repeated again for the aqueous layer with alkyl acetate till pyridine and/or pyridine derivatives content in aqueous layer [STREAM-1] is achieved <0.1%.

Further the obtained aqueous layer is heated under atmospheric pressure employing fractionating column. The precut consists of two layers, which is separated and the leftover free from pyridine bases can be easily disposed of, either by incineration or by suitably using in other processes. The organic layer of precut, enriched with alkyl acetate/alkanol is recycled for extraction after esterification of remaining alkanol into alkyl acetate as per process already established commercially. The aqueous layer of the precut is suitably incinerated.

The process described above in accordance with invention, the organic layer is distilled employing fractionating column. The dean stark assembly is also attached for the recovery of water layer. Small amount of water is present in the organic layer because of solubility of water in alkyl acetate. The precut consists of organic and aqueous layer. The water layer [STREAM-2] is mixed with aqueous layer [STREAM-1] obtained after final extraction, for the recovery of alkyl acetate/alkanol by distillation technique as discussed above. After isolation of precut, cut-1 [STREAM-4], which contains alkyl acetate with some alkanol is recovered. The quantity of intercut is maintained such that alkanol in recovered alkyl acetate used for next batch extraction is preferably maintained <0.2%. If the quantity of alkanol in cut 1 [STREAM 4] is >0.2%, this cut is mixed with STREAM-3 and added at water washing stage in the esterification process, for the recovery of alkyl acetate which is recycled at extraction stage.

Distillation is continued after the recovery of precut and cut-1 to recover solvent, which can be used for next batch extraction. The leftover mass after solvent recovery is further distilled employing fractionating column in steps as per established procedure industrially followed to recover pyridine and picolines of desired specifications.

Further, the present invention is illustrated in detail by way of the following examples. The examples are given herein for illustration of the invention and are not intended to be limiting thereof.

Example-1

Ammonia Reduction from Pyridine, β-Picoline Reaction Mass 2500 gm pyridine, β-picoline manufacturing reaction mass [% Pyridine -13.49, % picoline 5.49, % $NH_3$ 7.80; aliphatic amines, aldehyde and aldehyde based organic impurities, other monoalkyl pyridines, dialkyl pyridines, trialkyl pyridines or other unidentified heavy organic materials] was charged in a 5 liter round bottom flask, fitted with double surface condenser and $NH_3$ scrubber. The reaction mass was heated up to 85-95° C. till $NH_3$ content in pyridine-β-picoline reaction mass achieved <1.6%. After $NH_3$ recovery, 2300 gm of pyridine, β-picoline reaction mass [% pyridine-14.70, % β-picoline 5.93, % $NH_3$ 1.53] was obtained, which was suitable for extraction with ethyl acetate.

Example-2

Extraction of Pyridine and β-Picolines with ethyl acetate from Pyridine, β-Picoline Reaction Mass, after $NH_3$ Recovery Fresh ethyl acetate [295.0 gm] and pyridine, β-picoline reaction mass, [575 gm, % pyridine-14.70, % β-picoline 5.93, % $NH_3$ 1.53; aliphatic amines, aldehyde and aldehyde based organic impurities, other monoalkyl pyridines, dialkyl pyridines, trialkyl pyridines or other unidentified heavy organic materials] were charged in a two liter round bottom flask fitted with thermowell and double surface condenser. The mass was agitated for 30 minutes at room temperature and then it was transferred in a separating funnel for layer separation. The layers were separated and aqueous layer was analyzed for pyridine and beta-picoline content. The aqueous layer and the fresh ethyl acetate (135 gm) were recharged and the process was repeated. The pyridine and β-picoline in aqueous layer was achieved <0.1% [Stream-1] after total of nine extractions [Ethyl acetate 295 gm×1 and 135 gm×8].

Example-3

Recovery of Solvent Used for Extraction

Extracted organic layer [1503 gm] was charged in a 5 liter RBF equipped with glass column. [height 2 m, diameter 25 mm packed with S.S. structured packing], reflux divider and dean stark apparatus for separation of water layer. The mass was slowly heated to reflux temperature 70±5° C. and refluxing was maintained for 2-4 hrs. After the stabilization of the system, initially a precut was isolated which contained two layers. Aqueous layer [STREAM-2] contained water with ethyl alcohol (1-5%) and ethylamine and organic layer [STREAM-3] contains ethyl acetate (95%) with traces of ethyl alcohol (2-5%). Further, an intercut of ethyl acetate (90-95%) which contains ethyl alcohol (2-5%) was isolated [STREAM -4]. On further distillation, ethyl acetate [Assay 98%, ethyl alcohol <0.2%] was isolated for recycle in the extraction system. The left over mass, substantially free from water, was distilled employing fractional distillation technique as per industrially established process to isolate pyridine and beta picoline of desired specification.

Example-4

Recovery of Ethyl Acetate for Recycles in the Extraction System from Waste Streams STREAM-1 and STREAM-2 were combined together and distilled employing fractionating column [one meter length, diameter 25 mm, packed with SS structured packing]. The precut was collected up to 90-100° C. bottom temperature. It consists of two layers. The organic layer contains ethyl acetate (60-80%) and ethyl alcohol (15-30%) [STREAM-5]. The aqueous layer containing 2-4% ethyl acetate and 1-2% ethylamine can be incinerated. The leftover aqueous mass free from pyridine bases can be easily disposed off either by incineration or can be used in a suitable process for dilution purpose: STREAM -5 was recycled back after esterification for extraction.

Example-5

Recycle Study of Recovered Ethyl Acetate

To study the recycle with recovered ethyl acetate, 3 more batches of similar capacity were taken after necessary make up with the fresh ethyl acetate following the process mentioned above. Over all, total 1813 gm fresh ethyl acetate was used for 2500 gm pyridine, β-picoline reaction mass. Out of which 1183 gm ethyl acetate (Assay 98%, EtOH<0.2%) was recovered from extracted organic mass, which was recycled at EtOH<0.2%) was recovered from extracted organic mass, which was recycled at extraction stage. Including recovery from STREAM-1 to 5, total 1246 gm ethyl acetate was recovered as per process described above which was recycled at extraction stage. The solvent loss can be further minimized when the extraction is done following continuous mode of operation as major solvent loss is because of handling losses in batch mode.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

PROCESS FLOW DIAGRAM
SEPARATION OF PYRIDINE AND/OR PYRIDINE DERIVATIVES FROM AQUEOUS SOLUTIONS INCLUDING REACTION MASS AND RECOVERY/RECYCLE OF SOLVENT

EXTRACTION AND DISTILLATION

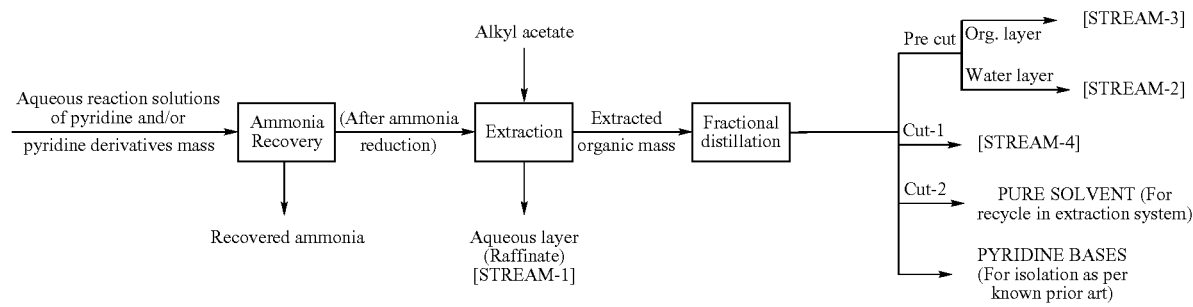

ISOLATION OF ALKYL ACETATE/ALKANOL FROM STREAM-1 & STREAM-2

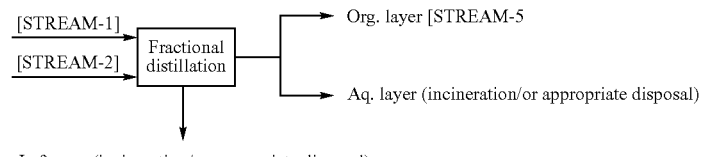

ESTERIFICATION AND RECYCLE OF ALKYL ACETATE/ ALKANOL FROM STREAM-3, STREAM-4 & STREAM-5

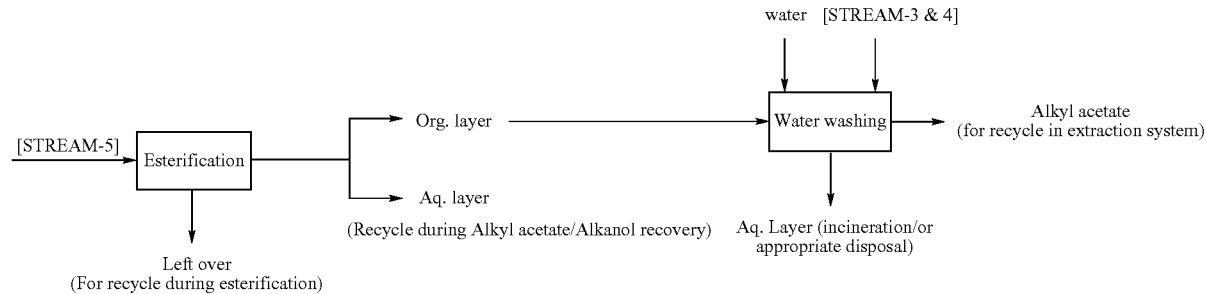

We claim:

1. An eco-friendly process for recovering pyridine and/or at least one derivative of pyridine from an aqueous mass and/or their manufacturing reaction mass, wherein the process comprises:
   extracting said aqueous mass and/or said manufacturing reaction mass with an alkyl acetate, to give an organic phase and aqueous phase;
   separating the organic phase and aqueous phase;
   distilling said organic phase to obtain the pyridine and/or the at least one derivative of pyridine,
   recovering said alkyl acetate by distilling and esterifying said aqueous phase and/or waste produced during said process, and/or by distilling and optionally esterifying said organic phase; and
   recycling said alkyl acetate thus recovered in said process.

2. The process according to claim 1, wherein said alkyl acetate is environmentally non-hazardous as per Class III of International Conference on Harmonization (ICH) guidelines.

3. The process according to claim 1, wherein said alkyl acetate is selected from the group consisting of ethyl acetate, n-propyl acetate, isopropyl acetate, and methyl acetate.

4. The process according to claim 3, wherein said alkyl acetate is ethyl acetate.

5. A process for recovering pyridine and/or at least one derivative of pyridine from their manufacturing reaction mass and/or an aqueous mass, comprising the pyridine and/or the at least one of derivative of pyridine, the process comprising:
   (B) extracting the manufacturing reaction mass and/or the aqueous mass with an alkyl acetate, to give an organic phase and an aqueous phase;
   (C) separating the organic phase and the aqueous phase, to obtain a separated organic phase and a separated aqueous phase;
   (D) distilling the separated organic phase, to obtain the pyridine and/or the at least one derivative, and to obtain distilled alkyl acetate;
   (E) recovering the alkyl acetate by
      (e1) distilling the separated aqueous phase and/or waste produced during the process, to obtain a distillate,
      (e2) esterifying the distillate, to obtain recovered alkyl acetate; and
   (F) recycling the recovered alkyl acetate and/or the distilled alkyl acetate, optionally subjected to esterification, into the treating (B).

6. The process according to claim 5, wherein the alkyl acetate is a Class III solvent under International Conference on Harmonization of Technical Requirements for Registration of Pharmaceuticals for Human Use (ICH) guidelines.

7. The process according to claim 5, wherein the alkyl acetate is selected from the group consisting of ethyl acetate, n-propyl acetate, isopropyl acetate, and methyl acetate.

8. The process according to claim 5, wherein the alkyl acetate is ethyl acetate.

9. The process according to claim 5, further comprising, before the treating (B):
(A) recovering ammonia from the manufacturing reaction mass by distillation.

* * * * *